United States Patent
Ladenson et al.

(10) Patent No.: US 7,615,218 B2
(45) Date of Patent: Nov. 10, 2009

(54) METHODS FOR DETERMINING AND LOWERING CAFFEINE CONCENTRATION IN FLUIDS

(75) Inventors: Jack Ladenson, St. Louis, MO (US); Ruth Ladenson, St. Louis, MO (US); Yvonne Landt, St. Louis, MO (US); Dan Crimmins, St Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 11/233,837

(22) Filed: Sep. 21, 2005

(65) Prior Publication Data

US 2007/0178524 A1    Aug. 2, 2007

Related U.S. Application Data

(60) Provisional application No. 60/612,662, filed on Sep. 24, 2004.

(51) Int. Cl.
*A61K 39/00* (2006.01)
*A61K 39/395* (2006.01)
*G01N 33/00* (2006.01)
*G01N 33/53* (2006.01)

(52) U.S. Cl. .............. 424/135.1; 424/130.1; 424/133.1; 435/4; 435/7.1; 435/7.94; 422/50; 422/56; 422/61

(58) Field of Classification Search .............. 435/4, 435/7.1; 422/56, 61; 424/135.1
See application file for complete search history.

(56) References Cited

U.S. PATENT DOCUMENTS

| 5,045,334 | A | * | 9/1991 | Kopsch et al. | 426/422 |
| 5,451,504 | A | * | 9/1995 | Fitzpatrick et al. | 435/7.2 |
| 5,610,072 | A | * | 3/1997 | Scherl et al. | 436/96 |
| 6,303,081 | B1 | * | 10/2001 | Mink et al. | 422/61 |

FOREIGN PATENT DOCUMENTS

WO    WO 02/085944 A2 * 10/2002
WO    WO-03/056163      7/2003

OTHER PUBLICATIONS

Ewert et al., Biochemistry (2002) 41:3628-3636.
Frenken et al., J. Biotech. (2000) 78:11-21.
Ghahroudi et al., FEBS Lett. (1997) 414:521-526.
Hamers-Casterman et al., Nature (1993) 363:446-448.
Perez et al., Biochemistry (2001) 40:74-83.
Spiller, Caffeine (1998) CRC Press, Table 9, p. 214, Boca Raton, New York.
Spiller, Caffeine (1998) CRC Press, pp. 13-33, Boca Raton, New York.
Spinelli et al., Biochemistry (2000) 39:1217-1222.
Van Der Linden et al., Biochim. Biophys. Acta (1999) 1431:37-46.
Van Der Linden et al., J. Immunol. Meth. (2000) 240:185-195.
International Search Report and Written Opinion for PCT/US05/34393, mailed Jul. 8, 2008, 13 pages.

* cited by examiner

*Primary Examiner*—Unsu Jung
(74) *Attorney, Agent, or Firm*—Morrison & Foerster LLP

(57) ABSTRACT

Single-chain, camelized heavy chain antibodies immunospecific for caffeine and stable at high temperatures are useful for analysis and recovery of caffeine in or from fluids. A device that provides a single-step lateral flow assay for caffeine and a useful peptide spacer are also described.

12 Claims, 6 Drawing Sheets

*T7 Tag*          1
GSH*MASMTGGQQMGRGSEFA*EVQLQASGGGLVQAGGSLRLSCTA

CDR 1                                CDR 2
S`GRTGTIYS`MAWFRQAPGKEREFLAT`VGWSSGIT`YYMDSVKGRF

CDR 3
TISRDNAKNSAYLQMNSLKPEDTAVYYC`TATRAYSVGYDY`WGQG

119      *E Tag*
TQVTVSH*AAAGAPVPYPDPLEPR*

Figure 2

SEQUENCE LISTING

<160> NUMBER OF SEQ ID NOS: 8

<210> SEQ ID NO 1
<211> LENGTH: 155
<212> TYPE: PRT
<213> ORGANISM: Artificial Sequence
<220> FEATURE:
<223> OTHER INFORMATION: Camelidae antibody

<400> SEQUENCE: 1

```
Gly Ser His Met Ala Ser Met Thr Gly Gly Gln Gln Met Gly Arg Gly
 1               5                  10                  15

Ser Glu Phe Ala Glu Val Gln Leu Gln Ala Ser Gly Gly Gly Leu Val
            20                  25                  30

Gln Ala Gly Gly Ser Leu Arg Leu Ser Cys Thr Ala Ser Gly Arg Thr
        35                  40                  45

Gly Thr Ile Tyr Ser Met Ala Trp Phe Arg Gln Ala Pro Gly Lys Glu
    50                  55                  60

Arg Glu Phe Leu Ala Thr Val Gly Trp Ser Ser Gly Ile Thr Tyr Tyr
65                  70                  75                  80

Met Asp Ser Val Lys Gly Arg Phe Thr Ile Ser Arg Asp Asn Ala Lys
                85                  90                  95

Asn Ser Ala Tyr Leu Gln Met Asn Ser Leu Lys Pro Glu Asp Thr Ala
            100                 105                 110

Val Tyr Tyr Cys Thr Ala Thr Arg Ala Tyr Ser Val Gly Tyr Asp Tyr
        115                 120                 125

Trp Gly Gln Gly Thr Gln Val Thr Val Ser His Ala Ala Ala Gly Ala
    130                 135                 140

Pro Val Pro Tyr Pro Asp Pro Leu Glu Pro Arg
145                 150                 155
```

<210> SEQ ID NO 2
<211> LENGTH: 138
<212> TYPE: PRT
<213> ORGANISM: Artificial Sequence
<220> FEATURE:
<223> OTHER INFORMATION: Camelidae antibody

<400> SEQUENCE: 2

```
Gly Ser His Met Ala Ser Met Thr Gly Gly Gln Gln Met Gly Arg Gly
 1               5                  10                  15

Ser Glu Phe Ala Glu Val Gln Leu Gln Ala Ser Gly Gly Gly Leu Val
            20                  25                  30

Gln Ala Gly Gly Ser Leu Arg Leu Ser Cys Thr Ala Ser Gly Arg Thr
        35                  40                  45

Gly Thr Ile Tyr Ser Met Ala Trp Phe Arg Gln Ala Pro Gly Lys Glu
    50                  55                  60

Arg Glu Phe Leu Ala Thr Val Gly Trp Ser Ser Gly Ile Thr Tyr Tyr
65                  70                  75                  80

Met Asp Ser Val Lys Gly Arg Phe Thr Ile Ser Arg Asp Asn Ala Lys
                85                  90                  95

Asn Ser Ala Tyr Leu Gln Met Asn Leu Lys Pro Glu Asp Thr Ala Val
            100                 105                 110

Tyr Tyr Cys Thr Ala Thr Arg Ala Tyr Ser Val Gly Tyr Asp Tyr Trp
        115                 120                 125
```

```
Gly Gln Gly Thr Gln Val Thr Val Ser His
    130                 135

<210> SEQ ID NO 3
<211> LENGTH: 135
<212> TYPE: PRT
<213> ORGANISM: Artificial Sequence
<220> FEATURE:
<223> OTHER INFORMATION: Camelidae antibody

<400> SEQUENCE: 3

Glu Val Gln Leu Gln Ala Ser Gly Gly Gly Leu Val Gln Ala Gly Gly
 1               5                  10                  15

Ser Leu Arg Leu Ser Cys Thr Ala Ser Gly Arg Thr Gly Thr Ile Tyr
            20                  25                  30

Ser Met Ala Trp Phe Arg Gln Ala Pro Gly Lys Glu Arg Glu Phe Leu
        35                  40                  45

Ala Thr Val Gly Trp Ser Ser Gly Ile Thr Tyr Tyr Met Asp Ser Val
    50                  55                  60

Lys Gly Arg Phe Thr Ile Ser Arg Asp Asn Ala Lys Asn Ser Ala Tyr
65                  70                  75                  80

Leu Gln Met Asn Ser Leu Lys Pro Glu Asp Thr Ala Val Tyr Tyr Cys
                85                  90                  95

Thr Ala Thr Arg Ala Tyr Ser Val Gly Tyr Asp Tyr Trp Gly Gln Gly
            100                 105                 110

Thr Gln Val Thr Val Ser His Ala Ala Ala Gly Ala Pro Val Pro Tyr
        115                 120                 125

Pro Asp Pro Leu Glu Pro Arg
    130                 135

<210> SEQ ID NO 4
<211> LENGTH: 119
<212> TYPE: PRT
<213> ORGANISM: Artificial Sequence
<220> FEATURE:
<223> OTHER INFORMATION: Camelidae antibody

<400> SEQUENCE: 4

Glu Val Gln Leu Gln Ala Ser Gly Gly Gly Leu Val Gln Ala Gly Gly
 1               5                  10                  15

Ser Leu Arg Leu Ser Cys Thr Ala Ser Gly Arg Thr Gly Thr Ile Tyr
            20                  25                  30

Ser Met Ala Trp Phe Arg Gln Ala Pro Gly Lys Glu Arg Glu Phe Leu
        35                  40                  45

Ala Thr Val Gly Trp Ser Ser Gly Ile Thr Tyr Tyr Met Asp Ser Val
    50                  55                  60

Lys Gly Arg Phe Thr Ile Ser Arg Asp Asn Ala Lys Asn Ser Ala Tyr
65                  70                  75                  80

Leu Gln Met Asn Ser Leu Lys Pro Glu Asp Thr Ala Val Tyr Tyr Cys
                85                  90                  95

Thr Ala Thr Arg Ala Tyr Ser Val Gly Tyr Asp Tyr Trp Gly Gln Gly
            100                 105                 110

Thr Gln Val Thr Val Ser His
        115

<210> SEQ ID NO 5
<211> LENGTH: 142
<212> TYPE: PRT
```

```
-continued

<213> ORGANISM: Artificial Sequence
<220> FEATURE:
<223> OTHER INFORMATION: Camelidae antibody

<400> SEQUENCE: 5

Glu Ala Glu Ala Glu Phe Ala Glu Val Gln Leu Gln Ala Ser Gly Gly
 1               5                  10                  15

Gly Leu Val Gln Ala Gly Gly Ser Leu Arg Leu Ser Cys Thr Ala Ser
            20                  25                  30

Gly Arg Thr Gly Thr Ile Tyr Ser Met Ala Trp Phe Arg Gln Ala Pro
        35                  40                  45

Gly Lys Glu Arg Glu Phe Leu Ala Thr Val Gly Trp Ser Ser Gly Ile
    50                  55                  60

Thr Tyr Tyr Met Asp Ser Val Lys Gly Arg Phe Thr Ile Ser Arg Asp
65                  70                  75                  80

Asn Ala Lys Asn Ser Ala Tyr Leu Gln Met Asn Ser Leu Lys Pro Glu
                85                  90                  95

Asp Thr Ala Val Tyr Tyr Cys Thr Ala Thr Arg Ala Tyr Ser Val Gly
            100                 105                 110

Tyr Asp Tyr Trp Gly Gln Gly Thr Gln Val Thr Val Ser His Ala Ala
        115                 120                 125

Ala Gly Ala Pro Val Pro Tyr Pro Asp Pro Leu Glu Pro Arg
    130                 135                 140

<210> SEQ ID NO 6
<211> LENGTH: 9
<212> TYPE: PRT
<213> ORGANISM: Artificial Sequence
<220> FEATURE:
<223> OTHER INFORMATION: Peptide spacer

<400> SEQUENCE: 6

Gly Gly Ser Gly Gly Ser Gly Gly Lys
 1               5

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ctcagtgaat tcgccgaggt ccagctgcag                                        30

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
ctgcaggaat ccttaacgcg gttccagcgg atccsgata                              39
```

METHODS FOR DETERMINING AND LOWERING CAFFEINE CONCENTRATION IN FLUIDS

RELATED APPLICATION

This application claims benefit of U.S. provisional application Ser. No. 60/612,662 filed 24 Sep. 2004 which is incorporated herein by reference in its entirety.

TECHNICAL FIELD

This invention relates generally to moieties that bind to caffeine and its derivatives at high temperature. The invention also relates to a method for determining the caffeine content of a fluid using such moieties as an analytical tool(s) and lowering the caffeine content of a fluid using such moieties as binding reagents. This invention also relates to a portable kit useful for determining the caffeine content of a fluid.

BACKGROUND ART

Caffeine, a cardiac stimulant and mild diuretic, is one of the world's most widely used drugs. Caffeine originates from the chemical family methylxanthine or xanthine which occur naturally in some plants. Beverages which are made from the nuts, leaves, stems, bark, of such caffeine containing plants are major sources of natural caffeine such as coffee made from the *Coffea arabica* plant and other caffeine containing plants, soft drinks including diet drinks made from Kola nuts, tea made from the leaves of *Thea sinensis* and cocoa used to make chocolate.

Caffeine is a food additive regulated by the U.S. Federal Food and Drug Administration ("FDA") and as such manufacturers of food and beverages are required to place the name caffeine on the food product label when caffeine has been added to the food product to prepare a caffeinated product. The FDA also regulates caffeine's use as a stimulant in some over the counter and prescription medicines.

The caffeine content of coffee, tea, soft drinks and medications containing caffeine varies widely. For example, an average five ounce cup of percolated coffee contains from about 40 mg to about 170 mg caffeine (Spiller, G. A., *Caffeine* (1998) CRC Press, Table 9, p. 214).

Whether due to increased focus on health or to the potential pharmacological effect of the consumption of caffeine, many people desire to know, at the time or prior to consumption of a fluid suspected of containing caffeine, whether or not that consumable fluid contains caffeine.

Currently, caffeine is measured by a variety of methods including ultraviolet spectroscopy, thin-layer chromatography, gas chromatography, high-performance liquid chromatography and capillary electrophoresis (Spiller, G. A. (Ed.), *Caffeine* (1998) 13-33, CRC Press, New York. However, none of these methods are readily applicable to home or restaurant use.

There are caffeine specific antibodies available, both rabbit polyclonal and mouse monoclonal. These traditional antibodies comprise heavy and light chains and have been shown to irreversibly denature at high temperatures (Van Der Linden, R. H. J., et al., *Biochim, Biophys. Acta* (1999); 1431:37-46; Ewert, S., et al., *Biochemistry* (2002); 41:3628-3636). These antibodies would not be applicable for caffeine determination at high temperature which may be convenient in some analytical settings.

Members of the Camelidae family have been shown to produce a form of antibody that is devoid of light chains (Hamers-Casterman, C., et al., *Nature* (1993) 363:446-448). The variable domains of such heavy-chain only antibodies ($V_{HH}$) have been cloned from peripheral blood lymphocytes from camel (*Camelus dromedarius*) (Ghahroudi, M. A., et al., *FEBS Lett.* (1997) 414:521-526) and llama (*lama glama*) (Van Der Linden, R., et al., *J Immunol Meth* (2000); 240:185-195). These single domain antibody fragments can refold (Pérez, J. M. J., et al., *Biochemistry* (2001) 40:74-83) and maintain functionality after thermal dissociation (van der Linden, R. H. J., et al., *Biochimica et Biophysica Acta* (1999) 1431:37-46; Ewert, S., et al., *Biochemistry* (2002) 41:3628-3636). In some cases, $V_{HH}$ fragments can bind specifically at temperatures up to 90° C. (Van Der Linden, R. H. J., supra (1999)). In addition, there are reports of hapten specific $V_{HH}$ fragments (Frenken. L. G. J., et al., *J Biotech* (2000); 78:11-21; Spinelli, S., et al., *Biochemistry* (2000) 39:1217-1222).

It is often convenient to test for caffeine at a high temperature and in this case reagents must be stable over a range of temperatures and provide accurate caffeine determination even if the detector system is heated.

Despite research in this area to accomplish these objectives, there remains a need for a dynamic, on location, "kit type," easy to use, straightforward, visual system to measure caffeine content of fluids, including hot fluids.

DISCLOSURE OF THE INVENTION

The invention provides heavy-chain, soluble, heat-stable antibodies specific for caffeine, as well as assays for caffeine detection and measurement that are adaptable for storefront, restaurant and home use, as well as applicable in analytical laboratories.

Thus, in one aspect, the invention is directed to caffeine-binding moieties operable at 70° C., in particular single-chain camelized heavy chain ($V_{HH}$) antibodies specific for caffeine. The invention antibodies successfully compete for caffeine and comprise the VSA2 amino acid sequence described below. Examples of such antibodies are represented by the amino acid sequences of SEQ ID NO's: 1-5.

In another aspect, the invention provides a rapid flow method for detecting caffeine, optionally in hot fluids. In one embodiment, the method employs a multizoned lateral or vertical flow device with zones in a same or substantially same plane which comprises a first zone, a second zone and a third zone. The device is designed so that a fluid is applied so as to flow sequentially through the first, second and third zones. The first zone comprises a mobile (i.e., releasable) labeled caffeine-binding moiety, the second zone comprises a stationary caffeine derivative and the third zone comprises a stationary polyclonal or monoclonal antibody or fragment that can bind to the caffeine-binding moiety released from the first zone. If caffeine is present in the applied fluid, it binds the labeled caffeine-binding moiety in the first zone, and thus prevents this moiety from binding to the stationary caffeine derivative in the second zone, and the moiety proceeds to the third zone. There it is captured by the antibody or antibody fragment that binds the caffeine-binding moiety liberated from the first zone. If caffeine is absent, the labeled moiety from the first zone is captured in the second zone by the caffeine derivative. By determining the presence or absence or amount of label in the second versus the third zone, the presence, absence, or amount of caffeine present in the fluid can be assessed. In one embodiment, the caffeine-binding moiety is the camelized $V_{HH}$ of the invention.

In one embodiment, the devices above-described can be included in a kit which can be designed to be mobile, disposable, and useable in homes and restaurants.

Thus, in another aspect, a single step method for selectively detecting and quantifying caffeine in a fluid sample suspected of containing caffeine comprises contacting a sample fluid with the device described above and determining the presence, absence or amount of label in the second and/or third zones.

Other aspects of the invention are directed to alternative formats for assessing caffeine in fluids using the camelized $V_{HH}$ single-chain antibodies of the invention, in particular ELISA formats.

In another aspect, the invention is directed to a method of extracting caffeine from a fluid containing extractable caffeine, which method comprises contacting the fluid with the antibodies of the invention linked to a solid support, optionally followed by eluting the caffeine from the support so as to allow reuse of the solid support or obtaining purified caffeine.

A kit can also be designed for removing caffeine from a fluid containing removable caffeine, wherein the kit contains the antibodies of the invention linked to a solid support. The kit can be mobile, disposable and useable in homes and restaurants.

In another aspect, the invention is directed to a derivatized peptide of 7-12 amino acids that is soluble and temperature stable, has a flexible and hydrophilic core devoid of aromatic amino acids and internal amines and carboxylates, and has a C-terminal residue capable of single-site reaction with a desired compound via EDC chemistry.

The derivatized peptide has a desired group coupled to the N-terminus, such as a label, or a specific binding agent such as biotin. If the compound to be conjugated is a carboxylate, the peptide contains an amino group on the amino acid at the C-terminus—for example, an amidated lysine at the C-terminus is particularly convenient. The amidation is necessary to avoid intramolecular coupling. This peptide is useful to confer a desired property on the compound coupled to the C-terminus.

BRIEF DESCRIPTION OF THE DRAWINGS

FIG. 2 (SEQ ID NO: 1) shows the deduced amino acid sequence that comprises the $V_{HH}$ antibody VSA2 expressed in pET28 vector with T7 Tag residues at N-terminus and vector E-Tag residues at the C-terminus. The 119 amino acids which comprise the $V_{HH}$ antibody VSA2 are noted as 1-119.

MODES OF CARRYING OUT THE INVENTION

Figure 1:
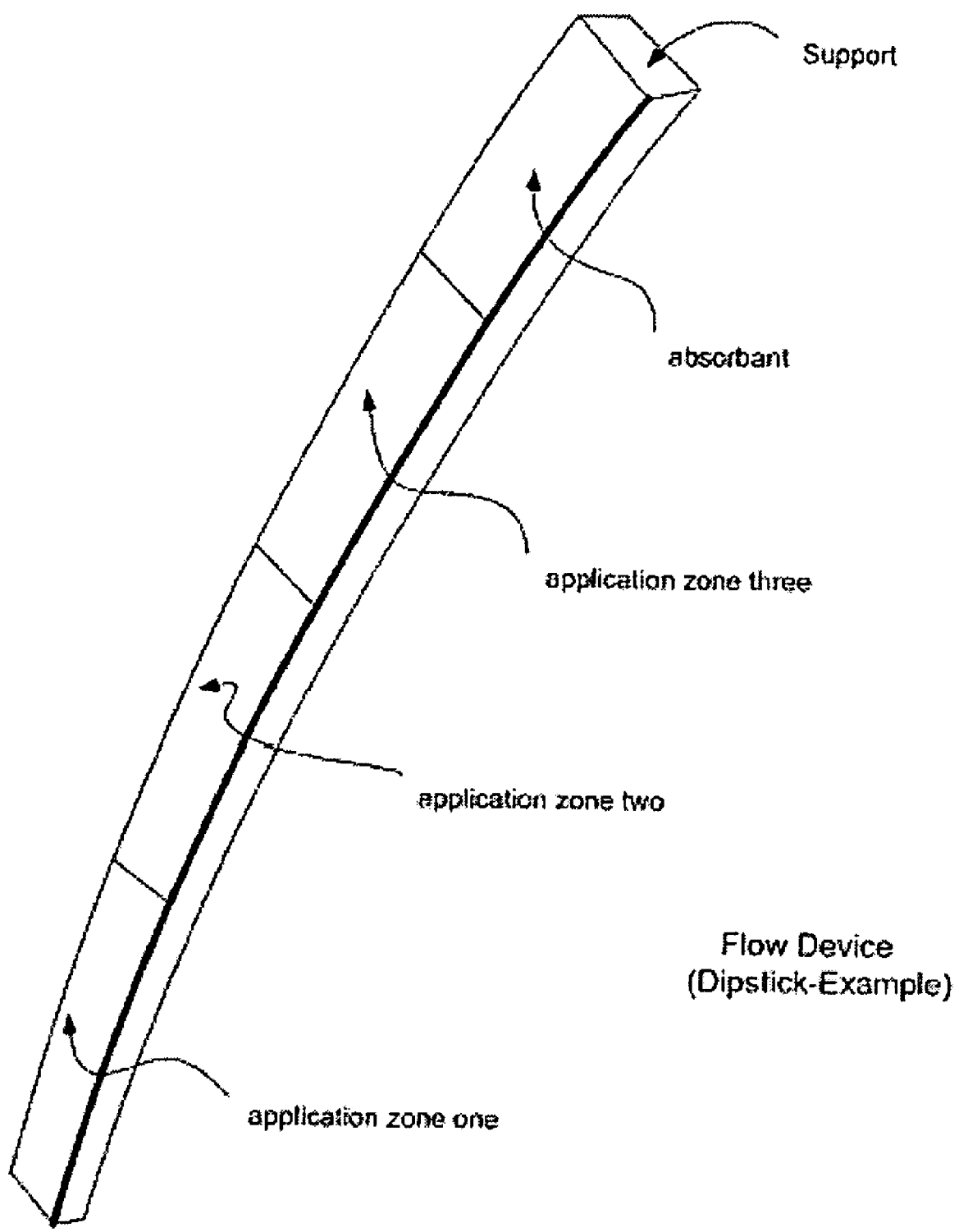
FIG. 1 is a depiction of an illustrative lateral flow device.

Unless otherwise defined, technical and scientific terms used herein have the meaning commonly understood by one of ordinary skill in the art. Methods and materials similar or equivalent to those described herein can be used in the practice or testing of the present discovery.

As used herein, "antibody" refers both to an entire immunoglobulin and to a useful fragment thereof, including recombinantly produced forms. Thus "antibody" includes Fab, $F_v$, and $F_{sv}$ forms, etc.

Similarly, "antibody fragment" includes any useful portion of an antibody which binds the same antigen that is recognized and bound by the intact or nonfragmented antibody. As noted above, "antibody fragment" also includes any synthetic or genetically engineered polypeptide that binds to a specific antigen.

The "single-chain camelized heavy chain antibodies" of the invention are single chain forms of antibodies that comprise at least the variable region of a heavy chain (symbolized $V_{HH}$) and have amino acid substitutions characteristic of camel (Ghahroudi, M. A., et al., *FEBS Letters* (1997) 414: 521-526) or llama (Vu, K. B., et al., *Mol Immunol* (1997) 34:1121-1131)-derived antibodies. For camel, these amino acid substitutions are Leu11 Ser, Val37Phe, Gly44Glu, Leu45Arg (or Cys) and Trp47Gly (or Leu) using the Kabat numbering system (Kabat, E., et al. (1991) *Sequences of Immunological Interest*, Fifth Edition, U.S. Department of Health and Human Services, Washington, D.C.). As further definition of the generic characteristic features of antibodies from the camelid family become available, these descriptions are incorporated into the meaning of "camelized" in describing the antibodies of the invention.

"Lateral flow device" includes a test strip, dip stick, lateral immunoassay device and the like; alternately, the flow of fluid through such devices may be horizontal, vertical, or at any angle. However, the device in general is a single strip of material or abutted pads of material that provide for continuous flow of liquid therethrough and may be supported by a more rigid backing.

As used herein with regard to a zone, the term "mobile" means that the reactive composition in the zone is readily moveable in the face of a fluid.

"Caffeine-binding moiety" refers to substances or compositions that specifically bind caffeine. One example of a caffeine-binding moiety is an antibody of the invention.

The term "anti-caffeine binder composition" refers to a substance or mixture that binds to a moiety which moiety specifically binds caffeine; typically, this anti-caffeine binder composition will comprise monoclonal or polyclonal antibodies or fragments that specifically bind the caffeine-binding moiety.

By "specific binding" to caffeine or to any target molecule is meant that the antibody or fragment or any moiety in general binds to caffeine (or alternative target) in preference to other substances present in the environment to an extent sufficiently greater for caffeine (or alternative target) than for the other substituents to provide the detection levels necessary for a meaningful result. As described in the examples below, the antibodies of the invention can detect caffeine even in the presence of closely related compounds.

"Contact" includes effectively mixing with and admixing, as well as simply placing in simple contact with.

"Fluid" in the context of the invention refers to liquids, usually aqueous-based liquids. Of most interest are liquids that may contain caffeine such as tea, coffee, caffeinated soft drinks, chocolate, and extracts of solid forms, such as caffeinated pills, coffee beans, etc. The fluid may be free-flowing or relatively viscous.

The Invention Antibodies

The invention provides novel antibodies useful for the analytical detection of caffeine in a fluid. As noted above, the antibodies contain at least the variable region of a heavy chain—i.e., they are represented as a single-chain form of an antibody which has characteristics of the heavy-chain antibodies derived from the camelid family. Thus, the antibodies of the invention are referred to as "camelized." Camelized antibodies have characteristic substitutions at particular positions as set forth in the definitions noted above. While the examples below describe a method for obtaining caffeine-specific antibodies by immunizing members of the camelid family and isolating the resulting antibodies using phage display techniques, alternative methods for obtaining such antibodies are available to the skilled artisan. For example, the heavy-chain variable regions of murine monoclonal antibodies currently immunospecific for caffeine can be modified to provide camelized characteristics by known genetic engineering techniques. The genes encoding the monoclonal antibodies can be recovered from the cells producing them and modified to provide suitable substitutions that result in the desired characteristics. One characteristic that is desirable in many contexts in which caffeine is to be measured is temperature stability. This appears inherent in the camelized forms and results in the ability of the antibodies to bind caffeine at relatively high temperatures. Thus, use of these antibodies can provide reliable results in testing fluids at least in the range of about 4° C. to about 70° C.

The deduced amino acid sequence of a caffeine-binding moiety isolated in the examples below comprises the amino acid sequence:

---

(SEQ ID NO: 1)
1
GSH*ASMTGGQQMG*RGSEFAEVQLQASGGGLVQAGGSLRLSCTA

S|GRTGTIYS|MAWFRQAPGKEREFLAT|VGWSSGIT|YYMDSVKGRF

TISRDNAKNSAYLQMNSLKPEDTAVYYC|TATRAYSVGYDY|WGQ
                                 119
GTQVTVSH*AAAGAPVPYPDPLEPR*.

---

The CDR regions are shown in brackets and the coded protein is numbered (1-119).

SEQ ID NO: 1 comprises not only the sequence derived from camelid antibodies, but also N-terminal and C-terminal tags (shown as underlined) that result from its recombinant production. Thus, the antibodies of the invention comprise embodiments which comprise the amino acid sequence of the antibody itself:

---

(SEQ ID NO: 4)
1
EVQLQASGGGLVQAGGSLRLSCTAS|GRTGTIYS|MAWFRQAPGKE

REFLAT|VGWSSGIT|YYMDSVKGRFTISRDNAKNSAYLQMNSLKP
                             119
EDTAVYYC|TATRAYSVGYDY|WGQGTQVTVSH,

--- or may comprise the amino acid sequence of the antibody with a N-terminus T7 Tag and some part of the vector:

---

(SEQ ID NO: 2)
1
GSH*ASMTGGQQMG*RGSEFAEVQLQASGGGLVQAGGSLRLSCTA

S|GRTGTIYS|MAWFRQAPGKEREFLAT|VGWSSGIT|YYMDSVKGRF

TISRDNAKNSAYLQMNLKPEDTAVYYC|TATRAYSVGYDY|WGQG
                             119
TQVTVSH

--- or may comprise the amino acid sequence of VSA2 plus a C-terminus E Tag:

---

(SEQ ID NO: 3)
1
EVQLQASGGGLVQAGGSLRLSCTAS|GRTGTIYS|MAWFRQAPGKE

REFLAT|VGWSSGIT|YYMDSVKGRFTISRDNAKNSAYLQMNSLKP
                             119
EDTAVYYC|TATRAYSVGYDY|WGQGTQVTVSHAAA

*GAPVPYPDPLEPR*

--- or may contain a C-terminus E-Tag with a NOT1 restriction site and additional sequence related to the METαA vector expressed in yeast:

---

SEQ ID NO: 5)
1                                  CDR 1
EAEAEFAEVQLQASGGGLVQAGGSLRLSCTAS|GRTGTIYS|MAWF
                      CDR 2
RQAPGKEREFLAT|VGWSSGIT|YYMDSVKGRFTISRDNAKNSAYLQ
                CDR 3                 119
MNSLKPEDTAVYYC|TATRAYSVGYDY|WGQGTQVTVSHAAA

GAPVPYPDPLEPR

---

The invention antibodies can be used in applications associated with specific binding for caffeine, including methods for preparation and purification or extraction of caffeine.

For use in purification, typically the antibodies are coupled to a solid support which is then contacted with a fluid containing caffeine. The caffeine, then bound to solid support, can be eluted if the object is purification or simply remain on the support if the object is removal of caffeine from the fluid.

For use in extraction, the antibodies of the invention may be coupled to a solid support including particulates which can be distributed throughout the fluid to be extracted and precipitated or otherwise separated, as, for example, by application of a magnetic field in the instance where the solid supports are magnetic particles. The solid supported antibodies of the invention are left in contact with the fluid for sufficient time to absorb the caffeine and then separated from the fluid. If recovery and measurement of the caffeine is desired, the caffeine may be eluted from the solid support.

Analysis Formats

In analytical uses, any standard assay format can be employed, including homogeneous and heterogeneous formats, labeling with enzymes, fluorescent molecules, or other appropriate labels, and any of the wide variety of immunoassay formats currently available in the art.

Particularly important formats for use of the antibodies of the invention as an analytical tool for caffeine employ the ELISA technique. In a particularly convenient form of this assay, the Competition Caffeine-ELISA, solid supports, such as microtiter plates are coated with caffeine and blocked using standard procedures. Then, the antibodies of the invention are mixed with serial dilutions of samples to be tested for caffeine and incubated to permit any caffeine in the sample to bind to available antibody(s). That antibody not bound to the caffeine in the solution, binds to the caffeine coated on the microtiter plate. The plates are washed, and bound antibody is detected by addition of a suitable tagged reagent, such as an antibody directed to the invention antibody itself having a labeling tag associated with it. Bound secondary antibody or reagent is then detected either by providing the secondary antibody directly with a label such as an enzyme or by providing an additional labeled reagent to detect the level of the invention antibody associated with the solid support. Many labels, such as enzyme labels, radioisotopes, fluorescent dyes, etc., can be employed in the same basic assay format. A specific embodiment of the Competition Caffeine-ELISA assay of the invention is described in Example 5, paragraph C, and its application to samples is described in Example 10.

Schematically, one embodiment of the assay may be represented as follows:

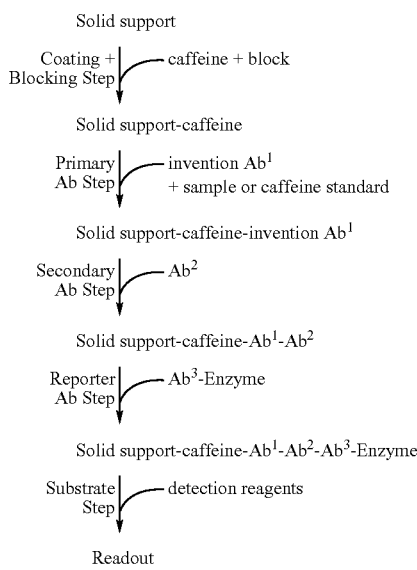

As will be apparent from the foregoing diagram, the greater the level of the caffeine in the sample or standard, the less $Ab^1$ will be available for capture on the solid support, and the corresponding readout will be less. As is also apparent, any binding reagents can be substituted for $Ab^2$ and $Ab^3$ as long as $Ab^2$ binds to $Ab^1$ and $Ab^3$ binds to $Ab^2$. Further, it is also apparent that $Ab^2$ could carry a label, rather than $Ab^3$, or, indeed, that $Ab^1$ of the invention could itself be labeled, and that labels other than enzymes might be used in a similar assay.

As noted above, this particular format does not limit the manner in which the invention antibodies are useful in immunoanalysis for caffeine, but represents a convenient format. These formats are readily packaged into kits containing the solid supports, possibly already coated with caffeine and blocked as well as standard caffeine solutions for controls and the antibodies of the invention along with label-detecting agents to permit successful readout.

The invention also provides a "lateral" flow device for detecting and determining the presence, absence or amount of caffeine or caffeine derivative in a fluid sample. The device comprises an absorbent strip or series of pads or materials on a backing which is capable of absorbing and transporting fluid via capillary or non-capillary action. The device can be a "dipstick" that provides a direct visual readout and determines the presence or absence of caffeine in a fluid, and can be single use and disposable. This embodiment is shown in FIG. 1.

While the antibodies of the invention are particularly useful as reagents in this device, the invention is also directed to the device and its method of use regardless of the nature of the caffeine-binding moiety employed.

The lateral flow device may be constructed to be user friendly, to require a very short time to provide a determined positive or negative qualitative result, and to have long-term stability over a wide range of operating temperatures including hot beverage temperatures. The lateral flow device may include a dipping section, or the fluid may be applied to the device using applicators or other systems. As described above, the lateral flow device contains at least three zones sequentially arranged to accommodate the flow of liquid from the first zone through the second zone and through the third zone. An absorbent zone may further be included downstream of the third zone, and an application zone may be included upstream of the first zone.

The first zone contains labeled caffeine-binding moiety, which, in some embodiments, is the antibody of the invention, or may be any antibody, polyclonal or monoclonal or fragment thereof specific for caffeine, or may be a peptidomimetic, aptamer, and the like. The requirement is simply that the moiety bind caffeine specifically and that it carry a label. The label may comprise a fluorophore, a radioisotope, a visible particle, such as latex, a plasmon resonance generating moiety, a dye, or even an enzyme (although an enzyme is considerably less convenient).

In an illustrative embodiment, the caffeine-binding moiety is labeled with an undecagold cluster of $Au_{11}$ and $Au_{13}$ which has a size as small as about 5 nm. U.S. Pat. No. 5,360,895 to Arimoto, et al., describes a useful process and method and reagents wherein antibodies or fragments thereof are covalently bound to a stable cluster of gold atoms. Such gold clusters may contain 11 or 13 atoms in their inner core, and are prepared by synthesizing a well defined organometallic compound containing sufficient gold atoms for visibility. The conjugates retain the antibody reactivity, availability, specificity and activity.

If the caffeine-binding moiety present in the first zone is an antibody, it may be produced recombinantly or may comprise antibodies produced by hybridomas or may be polyclonal antibodies immunospecific to caffeine. If the caffeine-binding moiety is produced recombinantly, a DNA comprising a nucleotide sequence encoding the caffeine-binding moiety is cloned into suitable vectors and produced in recombinant hosts. A wide range of recombinant hosts is known in the art; for convenience, the host may be E. coli or Pichia methanolica (Invitrogen) and an expression vector may include pET28 (Novagen) or pMETαA respectively. The caffeine-binding moiety may be purified, if desired, by affinity chromatography using caffeine as an adsorbent.

The second zone through which the liquid flows has a stationary caffeine derivative coupled thereto. If the temperature of the assay is elevated above room temperature, it is preferred that a simple conjugate of caffeine to a binding agent, such as biotin, optionally through a spacer be employed. At room temperatures, conjugates to KLH or BSA may be used.

Caffeine-BSA or caffeine-KLH may be produced using a functionalized form of caffeine such as 7-(5-carboxypentyl)-1,3-dimethyl xanthine as illustrated below. For high temperature determinations, it may be desirable to use such a simpler derivative to prevent denaturation of the BSA or KLH protein. One approach employs biotin coupled to caffeine through a spacer, in particular a peptide spacer. A peptide spacer is generally composed of small, relatively hydrophilic amino acids, such as glycine, serine, and the like. Lysine may be included in the peptide for ease of coupling, for example, to a carboxylated caffeine. Illustrated below is the peptide spacer Gly-Gly-Ser-Gly-Gly-Ser-Gly-Gly-Lys (SEQ ID NO: 6) which is coupled to caffeine through the ε-amino group of the lysine residue at the C-terminus.

The spacer peptide (SEQ ID NO: 6) is illustrative of a group of useful peptide spacers which separate a functional moiety coupled to the N-terminus of the spacer from a compound coupled at the C-terminus. Such spacers are useful for coupling to compounds that contain carboxyl groups for reaction with an amino group contained in the amino acid at the C-terminus, such as lysine. If the compound to be coupled to the C-terminal amino acid contains an available amino group, the C-terminal amino acid of the spacer may be either glutamate amide or aspartate amide for single site modification, or if the C-terminal amino acid lacks a carboxyl sidechain, the C-terminal carboxyl may participate in the coupling. The spacer peptide contains 7-12 amino acids and is derivatized at its N-terminus to a desired moiety, such as a label, a specific binding moiety, such as biotin, and the like. The amino acid sequence itself is devoid of aromatic side chains and of additional amino or carboxyl groups, and is flexible, hydrophilic, temperature-stable, and soluble. Convenient amino acids in the spacer peptide include glycine, serine, and threonine. If the compound to be bound contains an available carboxyl, it is desirable that the C-terminal amino acid comprise an amino group with an amidated carboxylate during the coupling reaction. Standard EDC chemistry or other diimide chemistry may be employed to couple the compound to the C-terminus.

Thus, in one illustration, the spacer peptide has the sequence set forth above as SEQ ID NO: 6; however, the sequence of glycine and serine residues may be rearranged, and the spacer may be extended or contracted to fit the boundaries of 7-12 amino acids.

The third zone contains an "anti-caffeine-binding composition," usually monoclonal or polyclonal antibody or fragment thereof that is specifically reactive with the caffeine-binding moiety employed in the first zone. This zone is also stationary and is designed to bind any caffeine-binding moiety that has transited the second zone. Antibodies can be raised to the caffeine-binding moieties in standard immunization protocols and produced as monoclonals, if desired, through standard immortalization technology, or may be produced recombinantly.

Zones two and three are constructed so that the reagents contained within them are stationary. This can be accomplished by passive absorption, although covalent bonding can also be used. A suitable binder may be employed with the zones so as to provide adherence.

The device thus provides capture lines in the second and third zones which are visually discernible and such that provide a positive or negative test result. If a visible band occurs in zone two, caffeine is absent. If a visible band occurs in zone three, caffeine is present.

The device can be modified to quantitate the level of caffeine by measuring the intensity of the visible bands in zones two and three. By running standards of known caffeine concentration, at least a qualitative measure of the level of caffeine can be deduced by comparing the intensities of the visible bands in zones two and three.

The lateral flow device has a region upstream of the first zone for contact with the fluid to be tested. Fluid flow may be horizontal, vertical, or at an angle, and may be induced by capillary action and/or, at least in the horizontal mode, by either capillary or non-capillary action through the device and an absorbent zone placed downstream of the third reactive zone.

The device may be included in a kit which contains all reagents for the determination of caffeine in a hot or cold fluid. It is useful in home testing, restaurant and fast food testing, rapid on site point of use testing and in general reliable qualitative testing for caffeine in a fluid.

With respect to the construction of the device itself, a multiplicity of constructions suitable for lateral flow is known in the art. See, e.g., U.S. Pat. Nos. 6,818,452; 6,689,618; 6,656,744; 4,943,522; 5,770,460; 5,798,273; and 4,855,240, to name but a few. For example, absorbent material that forms the strip or that covers a strip partially in zones two and three may be cellulose, derivatives of cellulose such as nitrocellulose, cellulose, or polyether sulfone or plastics having suitable fluid tolerance properties, and also of natural products which are insoluble in water or have been rendered insoluble in water and impervious to the fluid being analyzed. Polysulfones, nylons or other materials may also be employed. Porous plastics may also be employed such as those of polyethylene, polystyrene, polypropylene, PVC or Mylar®. When using nitrocellulose, it may be helpful to pretreat to render the membranes more hydrophilic.

The materials conducting the lateral (including vertical) flow may be adhered to a solid backing such as PVC or polystyrene to provide resilience and durability in handling the lateral flow device. Optionally, it may be desirable to include an absorbing area or flow termination area downstream of the third zone.

In an aspect this assay device is provided in the form of a kit. Typically such a kit will include one or more assay devices and instructions for the use of the devices. The instructions may provide directions to the user on how to apply sample fluid to the test strip and the amount of time needed to wait for analytical results to develop and details on how to read the kit results. A standard may also be included.

The following examples are offered to illustrate but not to limit the invention.

EXAMPLE 1

Preparation of Caffeine Derivatives

A. A caffeine carboxylate derivative, 7-(5-carboxypentyl)-1,3-dimethyl xanthine (Cook, et al., *J Pharmacol Exp Therapeutics* (1976); 199:679-686), was synthesized and analyzed by Daniels Fine Chemicals (Edmonton, Alberta). This caffeine derivative had a formula weight of 294.31 g/mole, melting point of 129° C., and the expected $^1$H-NMR spectrum.

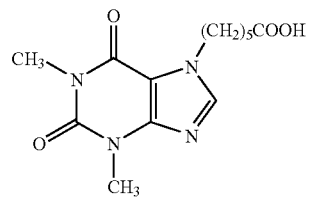

B. To obtain the immunogen, the caffeine derivative of paragraph A was covalently linked to Mariculture Keyhole Limpet Hemocyanin (KLH) following the Imject® Immunogen EDC (1-Ethyl-3-{3-dimethylaminopropyl}carbodiimide hydrochloride) Conjugation Kit protocol from Pierce Chemical (Rockford, Ill.). The protein conjugate was de-salted and buffer-exchanged into 0.083 M sodium phosphate, pH 7.2, containing 0.9 M NaCl prior to use as an immunogen. This caffeine-KLH conjugate has a $\lambda_{max}$ of 275 nm compared to 280 nm for KLH alone. The massive size of KLH (up to $1.3 \times 10^7$ Da) precluded further characterization.

C. A BSA conjugate was prepared using the EDC procedure described above to be used as a screening reagent for antibody assessment. Successful conjugation was confirmed as exemplified by retention time increase and peak broadening of the BSA-adduct in $C_{18}$RP-HPLC, and slower and broader electrophoretic migration in native gel electrophoresis. Matrix Assisted Laser Desorption Ionization Time-of-Flight Mass Spectroscopy (MALDI-TOFMS) spectra also demonstrates covalent coupling of the caffeine carboxylate derivative to BSA, showing 10 moles of covalently caffeine linked to each mole of BSA.

D. A soluble caffeine-biotinylated nonapeptide was designed with the formula: Biotin-Gly-Gly-Ser-Gly-Gly-Ser-Gly-Gly-Lys(amide) and synthesized using standard peptide synthesis procedures at Biomolecules Midwest, Inc., Waterloo, Ill. The crude peptide was purified following resin cleavage by preparative RP-HPLC and peak fractions were pooled and lyophilized. The carboxyl moiety of the caffeine derivative was coupled to the biotinylated nonapeptide at the ε-$NH_2$ group of the C-terminal lysine using EDC chemistry. The C-terminus was amidated to avoid any intramolecular bond formation between the ε-$NH_2$ of lysine with a normal C-terminal carboxylate and aromatic residues were omitted so as not to obfuscate the conjugate 250 nm-300 nm UV region so conjugation to caffeine could be readily followed. Corresponding peptides with a C-terminal acid-amide capable of reacting with amine groups using the same EDC chemistry may be designed based on this sequence.

The reaction mixture of the caffeine derivative and the biotinylated nonapeptide was purified by $C_{18}$RP-HPLC with fractions collected from 30 to 50 minutes at 0.5 minute intervals and monitored at 275 nm and 214 nm. The UV properties of the caffeine carboxylate derivative showed a red-shift from about 270 to 275 nm after conjugation (data not shown). The yield was estimated at 25-30% with a MALDI-TOFMS determined molecular weight of 1276.5 g/mole, compared to the expected value of 1276.6 g/mole.

In more detail, in a typical conjugation reaction, 4 mg of the nonapeptide was solubilized in 0.2 ml EDC conjugation buffer (Pierce Chemical, Rockford, Ill.) and combined with 2 mg caffeine derivative in 0.5 ml H2O. Then, 0.07 ml of EDC at 10 mg/0.1 ml water was added and the mixture incubated for two hours at room temperature. Analytical RP-HPLC Vydac (218TP54) was used to purify the desired product after acidifying the reaction mixture with 0.01 ml of 10% trifluoroacetic acid (TFA). A linear gradient form 0 to 60% B provided three distinct retention windows for the unreacted peptide, the unreacted caffeine derivative, and the bifunctional nonapeptide conjugate, with mobile phase A of 0.1% TFA and mobile phase B of 90% acetonitrile, 0.095% TFA using program 0'-10', 0% B; 10'-70', 0 to 60% B; at 1 ml/min and 37° C. Detection was at 214 nm and 275 nm using a photodiode array monitor.

Individual fractions were re-injected on $C_{18}$RP-HPLC to assess purity and also analyzed via Matrix Assisted Laser Desorption Ionization Time-of-Flight Mass Spectroscopy (MALDI-TOFMS) to determine molecular weight. An Applied Biosystems Voyager-DE™ STR instrument (850 Lincoln Centre Drive, Foster City, Calif., 94404 USA) was operated in the reflector, delayed extraction, positive linearity mode using an accelerating voltage of 20,000V, 68% grid voltage, 1.12% mirror voltage ratio, 400 ns extraction delay time, 2150 laser intensity, and 200 shots/spectrum. Samples were prepared by spotting 1 µl of matrix (10 mg/ml α-cyano-4-hydroxycinnamic acid in 50% acetonitrile and 0.1% TFA) on the stainless steel grid and allowed to air dry. Then, 1 µl of sample+matrix at a 1:4 volume ratio was applied to the grid and air dried. External calibration using the MS-CAL2 peptide mixture from Sigma Aldrich (3050 Spruce Street, Saint Louis, Mo. 63103, USA) provided an accuracy of about 1 part in 10,000.

EXAMPLE 2

Immunization of Camelids

Two types of camelids were immunized. Three llamas (Fanfare, Virtual and Very Senorita) were housed at Triple J Farms/Kent Laboratories, Bellingham, Wash. and two camels (Assab and Massawa) resided at the Veterinary Research Station, in Hagaz, Eritrea. The llamas each received an initial intermuscular (IM) injection of 250 µg of Caffeine-KLH in complete Freund's adjuvant (Sigma-Aldrich), followed by three boosts of 250 µg Caffeine-KLH in incomplete Freund's adjuvant (Sigma-Aldrich) at monthly intervals. The same schedule was used for the camels with MPL+TDM+CWS (Sigma-Aldrich) used as adjuvant for all injections. Test bleeds were taken at Day 0 (pre-immune) and 14 days after each of the first three immunizations (2, 6 and 10 weeks). One unit of blood (~500 mLs) collected with sodium citrate as anticoagulant (plus phosphate and dextrose, CPD) was taken one week after the final boost. All animal work was done under protocols approved by the Animal Studies Committee of Washington University in St. Louis.

Serum titers were determined using a microtiter plate ELISA with immobilized caffeine-BSA (Caffeine-ELISA). Caffeine-BSA at a concentration of 2 µg/ml in PBS was coated over night at 4° C. The wells were then blocked with PBS containing 2% non-fat dry milk (Blocker) for 2 h at 37° C. Dilutions of sera in Blocker were added and incubated for 90-120 min at 37° C. An anti-llama IgG-HRP conjugate (Bethyl Laboratories, Inc., Montgomery, Tex., USA) diluted 1/4000 in Blocker was added and incubated for 90-120 min at 37° C. This anti-llama antibody could also be used for screening camel sera. ABTS substrate was added and the absorbance read at 405 nm after color development. The wells were washed with TWEEN®/Saline between each step.

All five immunized camelids showed good immune response (data not shown). A process of selection, called panning, described in Examples 3 and 4, was utilized to isolate and enrich clones specific to caffeine.

EXAMPLE 3

Construction of Phage Display $V_{HH}$ Libraries

The units of blood from llamas and camels were processed within 24 and 48 h, respectively. Peripheral blood lymphocytes (PBL's) from each animal were isolated on density gradients using Histopaque® 1077 and 1088 (Sigma-Aldrich, 3050 Spruce Street, Saint Louis, Mo. 63103, USA). Messenger RNA (mRNA) was isolated from the purified PBL's using the FastTrack® 2.0 Kit (Invitrogen Corporation, Grand Island, N.Y.) and converted to $1^{st}$ strand DNA using the oligo dT primer of the cDNA Cycle® Kit (Invitrogen).

The variable regions of heavy chain immunoglobulins ($V_{HH}$) were amplified by nested PCR as described by Ghahroudi, M. A., et al., supra, using the initial primer pair CH2FORTA4 and VHBACKA6. The products were analyzed by agarose gel electrophoresis using 1.5% NuSieve® GTG. Gel plugs from the bands near 600/680 bp were used as template for the secondary PCR reaction utilizing primers VHBACKA4 and VHFOR36 (Ghahroudi, supra) which incorporate SfiI and NotI restriction sites on the 5' prime and 3' prime ends, respectively. The products were run on 1.25% (w/v) NuSieve® 3:1 preparative agarose gels and the band at 450 bp was extracted using Ultrafree-DNA filter system (Millipore, Bedford, Mass.). Each band is a pool of total amplified $V_{HH}$ cDNA.

The amplified $V_{HH}$ cDNA from each animal was incorporated into an M13 phagemid vector, pCANTAB 5E (Amersham Biosciences Corporation, Piscataway, N.J.), which links the $V_{HH}$ to one of the phage coat proteins. After growth and assembly of the phage, the $V_{HH}$ protein is displayed on the outside of the phage particle. In addition, a sequence of thirteen amino acids designated as the E-tag is added by the vector to the C-terminus of the $V_{HH}$ molecule.

Before incorporation into the vector, the $V_{HH}$ cDNA pools were digested by SfiI and NotI restriction enzymes and purified on StrataClean™ resin (Stratagene, La Jolla, Calif.). A 50 ng aliquot of each of the five restriction enzyme-digested $V_{HH}$ cDNA pools was ligated into 125 ng SfiI/NotI cut pCANTAB 5E using T-4 DNA ligase (Invitrogen). The ligated material was desalted and transformed into electrocompetent *Escherichia Coli* XL1-Blue MRF' cells (Stratagene). Six electroporations were done for each of the five ligations and pooled to form five separate bacterial libraries, one from each of the immunized animals. Library size was determined by plating an aliquot of the library and counting the resulting colonies. An extrapolation to the total volume of the library gives the total library size in colony forming units (cfu).

EXAMPLE 4

Selection of Caffeine Specific $V_{HH}$ Fragments

Phage-displayed caffeine specific $V_{HH}$ fragments were isolated by phage rescue and panning following the protocols of Harrison, J. L., et al, *Methods in Enzymology* (1996) 267:83-109. The transformed bacteria are grown to produce phage particles with displayed $V_{HH}$ fragments which are then incubated with immobilized caffeine-BSA as prepared in Example 1. A washing step removes unbound phage leaving those phage displaying caffeine-specific $V_{HH}$ fragments bound to the caffeine-BSA. The bound phage were eluted and used to infect TG1 bacteria. This represents one round of panning. This process is repeated with each round of panning showing further enrichment for specific binders. Single colonies from each round of panning were selected and grown for phage production as described (Harrison, supra). The success of the panning procedure to isolate specific binders was assessed by measuring binding of phage displayed $V_{HH}$ fragments to immobilized caffeine-BSA in a microtiter plate format (Phage Caffeine-ELISA) described below.

In more detail, a portion of each bacterial library was used to inoculate 100 ml 2×YT containing 100 μg/mL ampycillin and 1% glucose (2×YT+AG) and the culture grown with shaking at 37° C. to an A600 nm of 0.4-0.6. Ten ml of each culture was then infected with M13-K 07 helper phage (Amersham Pharmacia Bioscience, 800 Centennial Ave, Piscataway, N.J. 08855, USA) at a ratio of bacteria: helper phage of 1:5. Infection proceeded for 30 min at 37° C. without shaking and an additional 30 min at 37° C. with shaking. The infected cells were then pelleted by centrifugation at 3300×g for 10 min at 4° C., and gently resuspended in 50 ml 2×YT containing 100 μg/mL amp and 25 mg/mL kanamycin (2×YT+AK) and incubated with shaking overnight at 30° C.

The overnight culture was spun at 10,750×g for 10 min at 4° C. to pellet the bacterial debris. A solution of 0.2 g/ml PEG 6000 containing 2.5 M NaCl was added at a ratio of 1/5 to the supernatant containing the rescued phage. After mixing, the solution sat for 60 min or more at 4° C. allowing the phage to precipitate. The phage were collected by centrifugation at 10,750×g for 10 min at 4° C. and then resuspended in 2 ml PBS. The resuspended phage solution was centrifuged at 10,750×g for 2 min to remove any residual cellular debris.

Immunotubes (NUNC) were coated overnight at RT with 4 ml of 2 μg/ml caffeine-BSA in PBS. The tubes were rinsed 3× with PBS, then blocked with Blocker for 2 h at 37° C. or overnight at 4° C.

Two ml aliquots of the phage solutions were preincubated with 2 ml Blocker for 10 min at RT. The mixture was then added to the coated, blocked immunotubes. The tubes were incubated at RT for 30 min with rotation and for 90 min without rotation. The solutions containing unbound phage were discarded and the tubes were rinsed 10× with PBS containing 1 ml/L TWEEN® and 10× with PBS. The selected phage were eluted by adding 1 ml 100 mM triethylamine to the tubes and rotating them for 10 min at RT. The solution now containing eluted phage was added to a tube containing 0.5 mL 1 M Tris, pH 7.4 to neutralize the pH.

An overnight TG1 culture was grown in 2×YT at 37° C. with shaking, and was diluted 1/50 in fresh 2×YT and regrown to an A600 nm of 0.4-0.6. The eluted and neutralized phage was used to infect 8.5 ml of TG1 culture for a total volume of 10 mL. Additional TG1 cells were added to the immunotubes used for selection of phage so that any uneluted phage could infect the cells. Both cultures were incubated for 30 min at 37° C. without shaking, then combined. An aliquot was serially diluted and plated on SOBAG so that individual colonies could be tested for reactivity in the Caffeine ELISA assay. The remainder of the infected culture was spun at 3000×g for 10 min at 4° C., the precipitated cells were resuspended in 1 mL 2×YT and plated on a bioassay plate containing SOBAG. The plates were incubated overnight at 30° C. to grow ups cells for the next round of rescue and panning.

Subsequent rounds of panning were done similarly, except that only 50% of the precipitated phage was used, washings were increased to 20× each with PBS/TWEEN® and PBS, and only half of the eluted phage were used to reinfect. A portion of colonies from each round of panning was used to make a glycerol stock to be stored at −70° C. and the remainder used in the next round of panning.

Specific clones were selected by two rounds of panning. Table 1 shows details of the library sizes and panning results. One llama library produced no caffeine-specific clones. Preliminary affinity and thermal stability studies led to identification of one clone (VSA2) with better properties. To confirm the preliminary results, the TG1 cells were grown without kanamycin and with isopropy 1-beta-D-thiogalactopyranoside (IPTG) in order to get expressed protein not attached to phage. The expressed protein confirmed the preliminary results suggesting that VSA2 was the most promising clone.

TABLE 1

$V_{HH}$ Libraries Prepared from Immunized Camels[1] and Llamas[2]

| Immunized Animal | Library Size (cfu) | Positive Clones (by ELISA) | | |
|---|---|---|---|---|
| | | Pre-Pan | Round 1 | Round 2 |
| Assab[1] | 1 × 10⁶ | 0/96 | 0/48 | 2/48 |
| Massawa[1] | 4 × 10⁶ | 0/96 | 1/48 | 31/48 |
| Very Senorita[2] | 2 × 10⁵ | 0/96 | 17/48 | 37/48 |

TABLE 1-continued

V$_{HH}$ Libraries Prepared from Immunized Camels[1] and Llamas[2]

| Immunized Animal | Library Size (cfu) | Positive Clones (by ELISA) | | |
|---|---|---|---|---|
| | | Pre-Pan | Round 1 | Round 2 |
| FanFare[2] | 4 × 10⁵ | 76/96 | 0/48 | 0/48 |
| Virtual[2] | 1 × 10⁶ | 0/96 | 18/48 | 18/48 |

EXAMPLE 5

ELISA Assays

Three types of ELISA assays were performed to verify the presence of caffeine-binding V$_{HH}$ antibodies. In paragraph A, the antibodies as displayed on phage were assessed. In paragraph B, the V$_{HH}$ proteins not linked to phage particles were assayed for caffeine binding. In paragraph C, the expressed proteins were tested by a competition ELISA. A concise description of the three ELISA formats described herein is shown in Table 2.

TABLE 2

Summary of Three ELISA Formats

| Step | Phage Caffeine ELISA | Standard Caffeine ELISA | Competition Caffeine ELISA |
|---|---|---|---|
| Coating | Caffeine-BSA | Caffeine-BSA | Caffeine-BSA |
| Blocking | TBS/BSA | TBS/BSA | TBS/BSA |
| Primary Antibody | M13-Phage-displayed Llama V$_{HH}$ | Llama V$_{HH}$ | Llama V$_{HH}$ +/− caffeine standards or samples |
| Secondary Antibody | None | Mouse-anti-E-Tag | Mouse-anti-E-Tag |
| Reporter Antibody | Mouse-anti-M13-Horseradish Peroxidase Conjugate | Goat-anti-Mouse IgG-Alkaline Phosphatase Conjugate | Goat-anti-Mouse IgG-Alkaline Phosphatase Conjugate |
| Substrate | ABTS | p-npp | p-npp |

Note:
Abbreviations:
TBS, Tris buffered saline;
BSA, bovine serum albumin;
ABTS, [2,2'-azino-di-[3-ethyl-benzthiazoline-6-sulfonate];
p-npp, para nitro phenylphosphate A. Phage Caffeine-ELISA Microtiter plates were coated overnight at 4° C. with Caffeine-BSA at a concentration of 2 ug/ml in 50 mM Sodium Phosphate, pH 7.2, containing 150 mM NaCl (PBS)(Coating Step). The wells were then blocked with Blocker Buffer (PBS containing 2% non-fat dry milk) for 2 h at 37° C. (Blocking Step).

Phage from individual colonies diluted 1:2 in Blocker Buffer were added and incubated for 90-120 min at 37° C. (Primary Antibody Step). Bound phage were detected by the addition of mouse-anti-M13-antibody-HRP conjugate (Amersham Biosciences Corporation) diluted 1/1000 in 20 mM Tris, pH 7.2 containing 150 mM NaCl and 2% BSA (TBS/BSA) (Reporter Antibody Step) and ABTS substrate (Kirkagaard and Perry, Gaithersburg, Md.) (Substrate Step). The wells were washed with TWEEN®/Saline between each step and the reaction was monitored at A$_{405}$. The results for the five libraries are shown in Table 1.

B. Standard Caffeine-ELISA

After caffeine specific clones had been identified, soluble V$_{HH}$ proteins not linked to phage particles were expressed (Harrison, supra). Binding activity of the V$_{HH}$ proteins was assessed in a Standard Caffeine-ELISA. Microtiter plates were coated with caffeine and blocked as above (Coating and Blocking Steps). The V$_{HH}$ proteins serially diluted in 20 mM Tris. pH 7.2 containing 150 mM NaCl and 0.1% TWEEN® (TBS/BSA/TWEEN®) were added and incubated for 90 min at 37° C. (Primary Antibody Step). Bound V$_{HH}$ fragments were detected by the addition of a 1/1000 dilution in TBS/BSA/TWEEN® of mouse-anti-E Tag antibody (Amersham Bioscience Corporation) for 90 min at 37° C. (Secondary Antibody Step), followed by the addition of a 1/1000 dilution in TBS/BSA/TWEEN® of goat-anti-mouse IgG-alkaline phosphatase conjugate for 90 min at 37° C. (Reporter Antibody Step), before the addition of para-nitrophenyl phosphate substrate (p-npp) (Sigma Aldrich) (Substrate Step). The wells were washed and monitored at A$_{405}$ as above. The Standard ELISA assay was used to assess thermal stability and reactivity of VSA2 (Example 9, FIGS. 5 and 6).

C. Competition Caffeine-ELISA

Binding of V$_{HH}$ proteins to unconjugated caffeine was also assessed by a competition assay (Competition Caffeine-ELISA) in which 0-800 μg/mL caffeine (Sigma-Aldrich) was added as a competitor along with the V$_{HH}$ during the Primary Antibody Step of the Standard Caffeine-ELISA. All other steps are the same as for the Standard Caffeine ELISA. A$_{405}$ readings with and without competitor were compared. The competition ELISA was used to assess cross-reactivity of theophylline and theobromine (Example 9, FIG. 4) and also the amount of caffeine in various beverages (Example 9, FIG. 7, Table 3).

EXAMPLE 6

Selection of an Illustrative Clone

Four representative clones (2 llama and 2 camel) showed good competition with standard solutions of caffeine. Larger amounts of soluble antibodies from these clones were purified from the periplasmic fraction of one liter cell cultures (Harrison, supra) and further purified using an anti-E-Tag (Amersham Biosciences Corporation)-Sepharose affinity column following the manufacturer's protocol. The antibodies were assessed for thermal stability and reactivity. Clone VSA2 showed the best protein expression and the greatest degree of heat stability and was selected for further expansion and characterization.

$V_{HH}$ cDNA from the VSA2 clone in pCANTAB 5E was amplified using ABI PRISM Big Dye Terminator Cycle Sequencing Kit v3.1 (Applied Biosystems) and pCANTAB 5 Sequencing Primers S1 and S6 (Amersham Biosciences Corporation) and sequenced by an ABI automatic DNA sequencer. Data analysis was performed using Vector NTI software (Informax, North Bethesda, Md.). $V_{HH}$ cDNA from the VSA2 clone in the pET28 vector was amplified and sequenced as above, but using the T7 promoter primer (Promega, Madison, Wis.). The amino acid sequence was deduced from the DNA sequence, and is shown in FIG. 2.

The sequence of VSA2 was compared with published llama sequences (Harmsen, M. M., et al., *Mol. Immunol.* (2000) 37:579-590). Based on key residues in the framework and CDR regions, this $V_{HH}$ is a member of the VHH1 subfamily. FIG. 2 also shows the Complementary Determining Regions (CDR's), which when properly folded combine to form the antigen binding site, enclosed in boxes. The underlined N-terminal and C-terminal extensions were incorporated by the pET28 and pCANTAB 5E vectors, respectively. The E-Tag and T7 Promoter Tag amino acids are in italics.

EXAMPLE 7

Production and Purification of VSA2 from *E. coli*

VSA2 was cloned into pET28a vector (Novagen, Madison, Wis.) at the EcoR1 site and transformed into chemically competent *Escherichia coli* BL21 Star™ (DE3)pLysS cells (Invitrogen Corporation). This vector incorporates a HisTag sequence and nineteen additional amino acids encompassing the T7 promoter Tag at the N-terminus. The expressed VSA2 was purified from lysed cells utilizing NiNTA agarose (Qiagen, Valencia, Calif.). After thrombin cleavage to remove the HisTag, the VSA2 was dialysed against PBS and stored in aliquots at −20° C. Typically, one liter of culture yielded 4 mg $V_{HH}$ protein.

Purified VSA2 (0.1-0.5 µg) was run in three lanes on 10-20% SDS-PAGE. One lane was stained with Coomassie Blue for total protein visualization. The two other lanes were transferred to a PVDF membrane (Dieckgraefe, B. K., et al., *J Investig. Med.* (2002) 50:421-434) and probed with goat-anti-llama IgG (Bethyl Laboratories, Inc., Montgomery, Tex.) or mouse-anti-E-Tag, followed by rabbit-anti-goat IgG or goat-anti-mouse IgG alkaline phosphatase conjugate (Sigma-Aldrich), respectively. All antibodies were diluted 1/1000 in TBS/BSA. The signal was developed with BCIP/NBT substrate (Kirkagaard and Perry, Gaithersburg, Md.). Molecular weight markers were run in tandem with each of the VSA2 lanes. In addition, the molecular weight of the purified VSA2 was determined by MALDI-TOFMS and compared to the calculated expected value.

Figure 3:
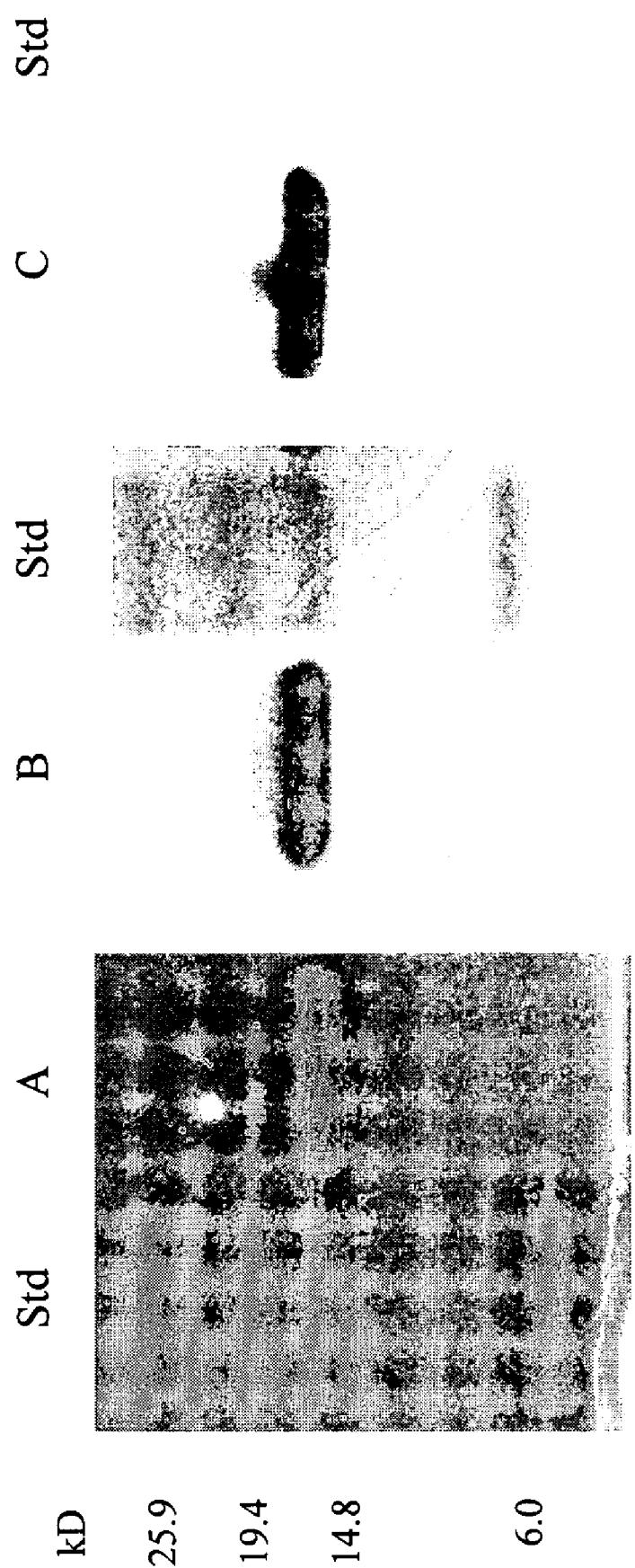
FIGS. 3A-3C show the results of SDS-PAGE analysis of a protein encoded by the VSA2 clone.

SDS-PAGE and Western blots of purified VSA2 are shown in FIG. 3. Panel A: SDS-PAGE of 0.5 µg VSA2 run on a 10-20% gradient gel and stained with Coomassie Blue, Panel B: Western Blot of 0.5 µg VSA2 transferred to PVDF membrane and blotted with goat-anti-llama IgG followed by rabbit-anti-goat IgG and developed with BCIP/NBT substrate, Panel C: Western Blot of 0.1 µg VSA2 transferred to PVDF membrane and blotted with mouse-anti-E-Tag, followed by goat-anti-mouse IgG alkaline phosphatase conjugate and developed with BCIP/NBT substrate, Std: Molecular weight (kD) markers run in tandem with each lane of VSA2. Coomassie blue staining of VSA2 shows a single band at ~15 kD (Panel A). This band corresponds to the Western blot reactive bands using two different capping antibodies, anti-llama IgG (Panel B) and anti-E-Tag (Panel C). In addition, an immunostained band with identical mobility was observed following anti-T7-Tag Western blot (data not shown). These results validate the protein as a llama derived antibody fragment and show full-length expression from the N-terminal T7 Promoter Tag to the C-terminal E-Tag (SEQ ID NO: 1).

Molecular weight determination of VSA2 by MALDI-TOFMS gave a value of 16,603.2, which agrees well with the expected MW of 16,600.1. Along with the gel data above, this confirms the $V_{HH}$ identity and purity.

EXAMPLE 8

Production and Purification of VSA2 from Yeast

In order to produce a larger amount of VSA2 without the HisTag, the VSA2 sequence was cloned into the pMETαA vector (Invitrogen, Carlsbad, Calif.) for expression in yeast (*Pichia Methanolica*, Invitrogen, Carlsbad, Calif.). Initial PCR of VSA2 insert with ECOR1 sites on both the 3' and 5' ends used the VSA2-pCANTAB as the template. Primers were:

Forward-CTC AGT GAA TTC GCC GAG GTC CAG CTG CAG (SEQ ID NO: 7)

Reverse-CTG CAG GAA TCC TTAA CGC GGT TCC AGC GGA TCCS GATA (SEQ ID NO: 8)

The PCR products were separated on a 1% agarose gel and purified using the QIAEXII gel extraction kit (Qiagen, Inc.; Valencia, Calif.). The ECOR1 sites were exposed by digestion with ECOR1, 20 units of enzyme per 5 ug DNA, 37° C. for 4 hours. After digestion, the ECOR1 was removed by running the DNA on a 1% agarose gel, and purifying the DNA insert using the QIAEXII gel extraction kit. The pET28a vector (Novagen, EMD Biosciences, Inc., Madison, Wis.) was cut with ECOR1 and dephosphorylated using shrimp alkaline phosphatase. The ECOR1 digests were set up as follows: 20 units of enzyme per 5 ug DNA, incubation 37° C. for 4 hours. Dephosphorylation reaction was set up as follows: 10 units of shrimp alkaline phosphatase per 300 ng DNA, incubation 37° C. for 30 minutes. The shrimp alkaline phosphatase was heat inactivated by heating at 65° C. for 15 minutes. The digested dephosphorylated pET28a was run on a 1% agarose gel and the excised DNA was purified using a Genecleane® II kit (MP Biomedicals, Solon, Ohio.).

The VSA2 insert was ligated into the ECOR1 cut pET28a vector and transformed into top 10 cells (Invitrogen, Carlsbad, Calif.). The presence of the insert was confirmed by restriction digest analysis and the resulting clones sequenced using ABI Prism BigDye® Terminator V3.1 (Applied Biosystems, Foster City, Calif.).

The VSA2 sequence was excised from the VSA2-pET28a construct by digestion with ECOR1. The digest was set up as follows: 20 units of enzyme per 5 ug DNA, incubation 37° C.

for 4 hours. The DNA was separated on a 1% agarose gel and the VSA2 insert was purified using the QIAEXII gel extraction kit. The pMETαA vector was cut with ECOR1 and dephosphorylated using shrimp alkaline phosphatase. The ECOR1 digest was set up as follows: 20 units of enzyme per 5 µg DNA, incubation 37° C. for 4 hrs. The dephosphorylation reaction used 10 units of shrimp alkaline phosphatase per 300 ng DNA, incubated at 37° C. for 30 minutes. The shrimp alkaline phosphatase was then heat inactivated by heating at 65° C. for 15 minutes. The digest dephosphorylated pMETαA vector was run on a 1% agarose gel and the excised DNA was purified using a Genecleane® II Kit.

The ECOR1 cut VSA2 insert was ligated into the ECOR1 cut pMETαA vector and transformed into top 10 cells. The presence of the insert was confirmed by restriction digest analysis and the resulting clones sequenced using ABI Prism BigDye® Terminator v3.1 Cycle Sequencing Kit (Applied Biosystems, Foster City, Calif.).

The expression cassette was excised using AscI restriction digest and transformed into electrocompetent PMAD II cells. The resulting clones were screened for expression of VSA2 on SDS-PAGE. High expressing clones were identified and protein purification was scaled up as follows:

Fifty ml of Buffered Complex Dextrose Medium (BMDY, Recipe P. Methanolica Expression Kit. Version B Instruction Manual, Invitrogen, Carlsbad, Calif.) was inoculated with a single yeast colony and grown overnight at 30° C. with shaking at 250 rpm. One liter of fresh BMDT (Invitrogen, Supra) was inoculated with 5 ml of the overnight culture and grown 16 to 18 h at 30° C. with shaking at 250 rpm until the A600 nm was between 2 and 10. The yeast cells were harvested by centrifugation at 1500×g for 6 min and the cells then were resuspended in 250 mL of Buffered Methanol Complex Medium (BMMY). After 24 h of growth at 30° C. with shaking at 250 rpm, the culture was supplemented with 1.25 mL methanol to give a final concentration of 0.5% methanol. The methanol supplemented media containing the secreted protein was then harvested 48 hr post induction and cleared by centrifugation at 1500×g for 6 min. The harvested medium was stored at −20° C. until purification.

The VSA2 was purified using a BSA-caffeine affinity column. Fractions containing VSA2 were dialysed overnight against PBS, and then frozen at −80° C. A typical yield was 2 mg VSA2 per 50 ml harvested medium. The resulting product contains the VSA2 sequence with the addition of the NOT1 site and thirteen amino acid E-tag at the C-terminus and seven amino acids at the N-terminus related to the vectors utilized (SEQ ID NO: 5). MALDI-TOFMS gave a molecular weight of 15,345.2 compared to the expected of 15,340.2).

All the characterizations of VSA2 made in yeast (thermal stability, reactivity, cross-reactivity, etc.) were virtually identical as the characterization of the VSA2 made in *E. coli* shown in Example 9 (data not shown).

EXAMPLE 9

Characterization of VSA2

A. Cross-Reactivity of Common Caffeine Competitors

Two additional methylxanthines with similar structure to caffeine, theobromine and theophylline, were tested for cross-reactivity with VSA2. The Competition Caffeine-ELISA described above was run using theobromine and theophylline (Sigma-Aldrich) as competitors at concentrations up to 250 µg/mL and compared to competition by caffeine.

Figure 4:
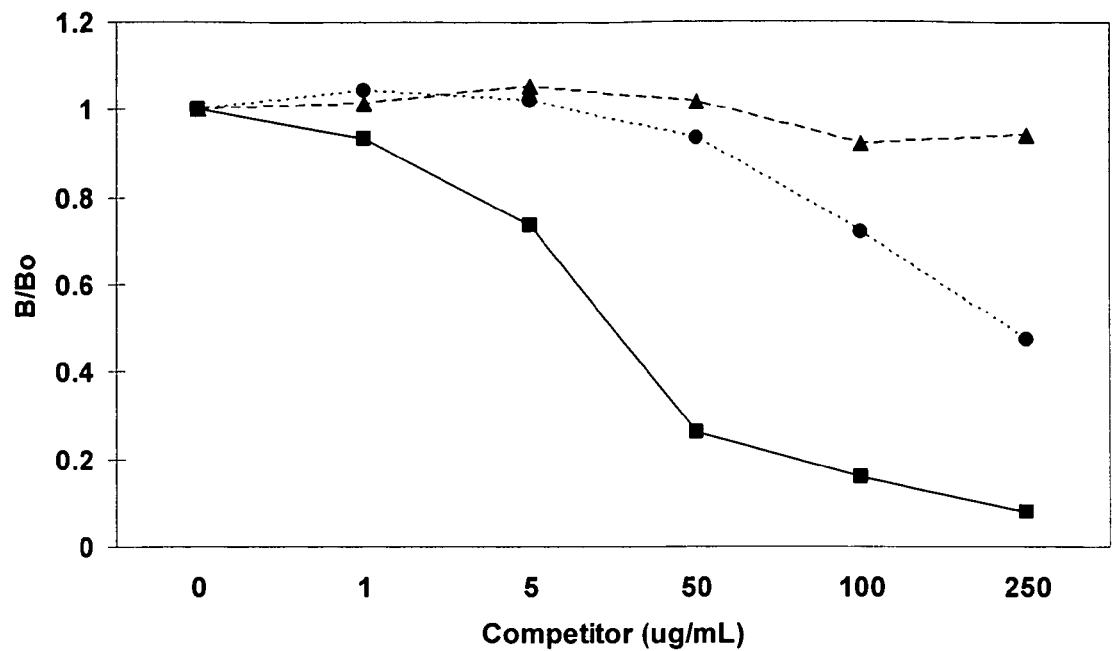
FIG. 4 shows the results of a competition assay showing the specificity of the $V_{HH}$ antibody VSA2 with respect to closely related compounds theophylline and theobromine.

The results of the competition caffeine-ELISA run with increasing concentrations of caffeine (-■-), theophylline (. .●. .) or theobromine (- -▲- -) is shown in FIG. 4. The response (B) was compared to that of no competitor (Bo). As shown, VSA2 is highly specific for caffeine.

Theophylline and theobromine are structurally related to caffeine and are common competitors. Theophylline at 250 µg/mL does exhibit some competition with VSA2, but approximately fourteen times as much theophylline as caffeine is needed for equivalent competition which gives a cross-reactivity of 7.4%. Theobromine at concentrations up to 250 µg/mL shows essentially no competition with VSA2. The two commercially available mouse monoclonal antibodies used in this study are reported to have cross reactivities of 11.4% and 3.0% with theophylline and 2.1% and 2.7% with theobromine (Biodesign International, Specification Sheets). Thus, VSA2 showed cross reactivity comparable to the mouse monoclonal antibodies. Theophylline and theobromine are present in coffee at approximately 1 µg/mL (compared to caffeine of 350-1,200 µg/ml) (Spiller, G. A., *Caffeine* (1998) CRC Press, N.Y.)while standard cola drinks contain less than 0.1 µg/mL of these substances (internet address: archive.food.gov.uk/maff/archive/food/infsheet/1997/no103). Various tea products are reported to contain 2 µg/ml or less of theophylline, but from 6-31 µg/mL theobromine compared to 245-430 µg/ml caffeine (internet address: archive.food.gov.uk/maff/archive/food/infsheet/1997/no103, supra). Thus the caffeine concentration in these beverages can be determined in our assay without interference from theophylline or theobromine.

B. Thermal Stability and Reactivity

The thermal stability of VSA2 was determined and compared to that of two mouse anti-caffeine monoclonal antibodies (Catalog No. G45110 M and G45111 M, U.S. Biological, Swampscott, Mass.). Antibody solutions were prepared in TBS containing 0.1% TWEEN® and incubated for 20 min at temperatures ranging from RT to 90° C. The solutions were re-equilibrated to RT before measuring caffeine binding activity. For VSA2, the Standard Caffeine-ELISA protocol was followed. For the commercial mouse monoclonal antibodies, the Secondary Antibody Step was skipped.

Figure 5:
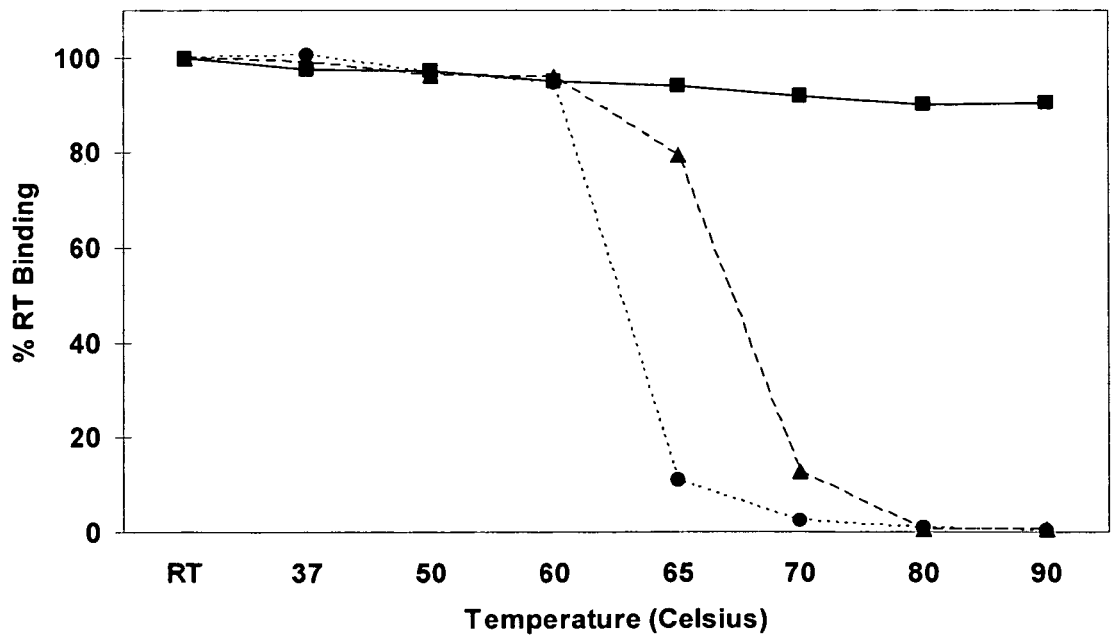
FIG. 5 is a graph showing the comparison of temperature stability of the $V_{HH}$ antibody of the invention as compared to murine anti-caffeine monoclonal antibodies.

FIG. 5 compares the binding in the Standard Caffeine-ELISA of VSA2 (- -■- -) with that of two mouse anti-caffeine monoclonal antibodies, MAb1 (. .●. .) and MAb2 (- -▲- -), after incubation at temperatures from RT to 90° C. for 20 minutes. At temperatures of 60° C. and below there is no effect on either the llama $V_{HH}$ or the mouse monoclonal antibodies. However, at higher temperatures the $V_{HH}$ shows much greater stability compared to the mouse monoclonal antibodies. The $V_{HH}$ retains greater than 90% of its activity after pretreatment at temperatures up to 90° C., whereas virtually all of the binding activity of the mouse antibodies is lost at 70° C. and higher.

The thermal reactivity of VSA2 was also determined. VSA2 and the soluble caffeine-biotinylated nonapeptide (0, 20 and 200 µg/ml) described in Example 1 were mixed and incubated in a 70° C. water bath for 20 min. (Immobilized caffeine-BSA and BSA carrier protein could not be used at these temperatures.) Streptavidin coated magnetic beads (Dynabeads®MyOne™Streptavidin, Dynal Biotech Inc., Lake Success, N.Y.) were added and the mixture incubated at 70° C. to allow the caffeine-biotinylated nonapeptide and any VSA2 bound to it to attach to the beads. The beads were pelleted using a magnetic device according to the manufacturer's recommendation to separate the bound from the unbound VSA2. The amount of unbound VSA2 remaining in the supernatant was determined in a Standard Caffeine-ELISA.

Figure 6:
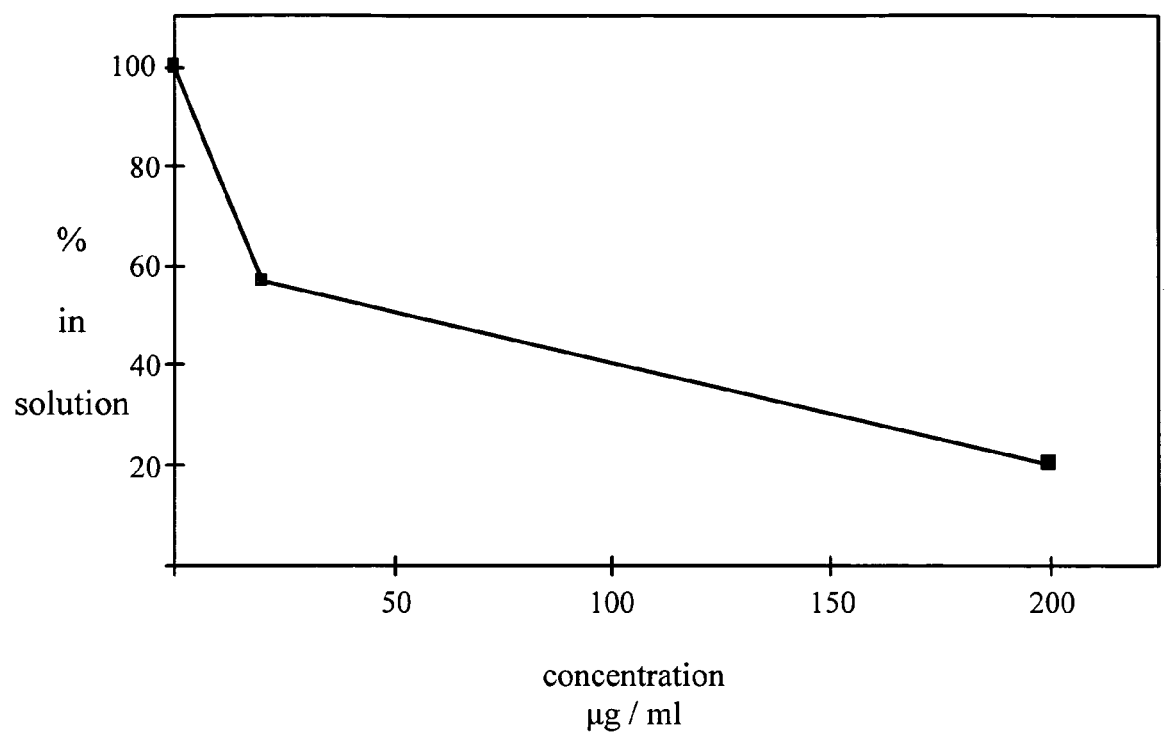
FIG. 6 shows the reactivity of VSA2 at 70° C.

FIG. 6 shows the amount of VSA2 remaining after incubation at 70° C. with increasing concentrations of the caffeine-biotinylated-nonapeptide conjugate and removal of the VSA2-biotinylated caffeine-nonapeptide complex by streptavidin coated magnetic beads. At added concentrations of 20 and 200 μg/mL of caffeine-biotinylated-nonapeptide, 56.8% and 20.1%, respectively, of the $V_{HH}$ remains in solution. This indicates that VSA2 is able to bind to caffeine at elevated temperatures.

EXAMPLE 10

Determination of Caffeine Concentrations in Beverages by Competition Caffeine-ELISA Regular and decaffeinated coffee (Seattle's Best™) was obtained from Aramark, St. Louis, Mo. Regular and caffeine-free Coca-Cola Classic® and Diet Coke® were purchased from vending machines at Barnes-Jewish Hospital (St. Louis, Mo.).

Stock solutions of caffeine (Sigma-Aldrich) at 5 mg/mL were prepared in either TBS, decaffeinated coffee, caffeine free Coca-Cola Classic® or caffeine free Diet Coke®. Caffeine standards from 0-800 μg/mL were prepared using the above as diluents. Caffeinated beverages were assayed neat, and serially diluted 2-fold. Decaffeinated coffee, caffeine-free Coca-Cola Classic® or caffeine-free Diet Coke® were used as diluent for coffee, Coca-Cola Classic® or Diet Coke®, respectively. Decaffeinated coffee was assayed neat and compared to standards diluted in TBS. The standards and beverages were incubated for 30 min at RT with equal volumes of VSA2 diluted to 2 μg/mL in 40 mM Tris, pH 7.2, containing 300 mM NaCl, 4% BSA and 0.1% TWEEN®-20. The preincubated mixtures were added to the Standard Caffeine-ELISA at the Primary Antibody Step. The assay was very matrix dependent, i.e., dilution of coffee or soda in buffer did not give parallel competition to that of caffeine standards. Therefore, we used decaffeinated coffee or caffeine-free soda as diluent in assays of coffee and soda, respectively. Samples were compared only to standards prepared in the same diluent. A logit/log transformation was used to linearize the data.

Figure 7:
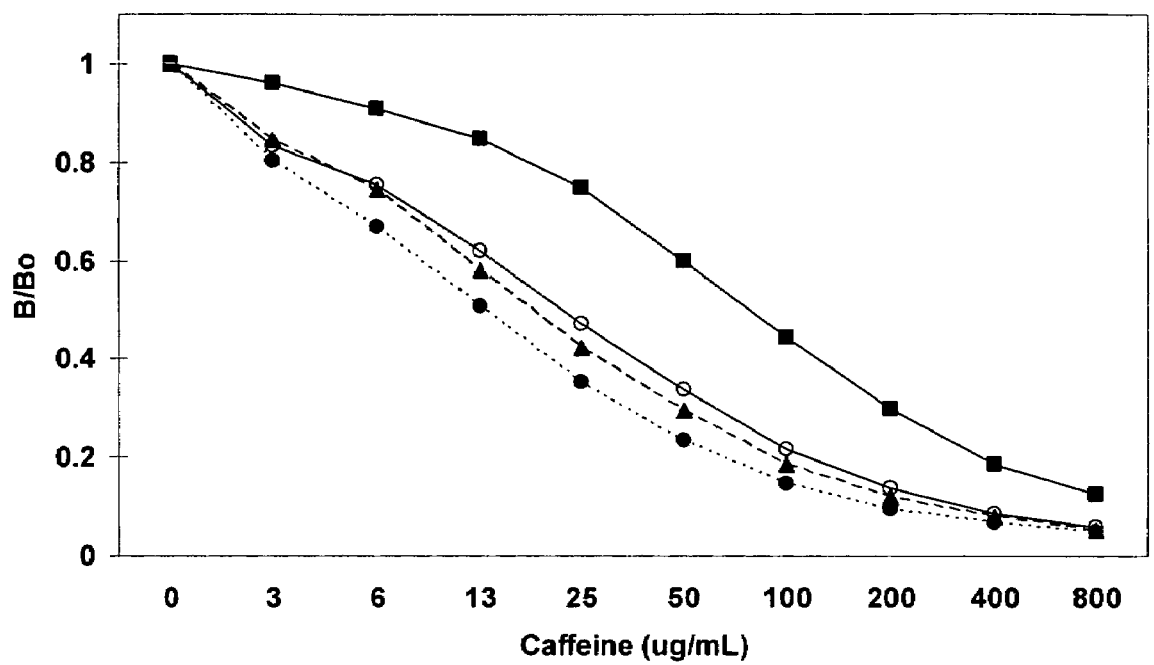
FIG. 7 shows standard curves obtained in the ELISA competition assay for caffeine concentration for various diluents.

FIG. 7 shows standard curves of competition caffeine-ELISA's showing effects of different diluents. Caffeine was diluted with decaf coffee (-■-), Classic Coke® (. .●. . ), Diet Coke® (- -▲- -) or TBS (-○-) to produce standard concentrations of 0-800 μg/mL). Competition was determined by comparing the dose response at each concentration (B) to that of no competitor (Bo). Each point represents the median of three determinations.

The results obtained in this assay were compared with those obtained from HPLC.

Theophylline and caffeine standards were purchased from Sigma-Aldrich having nominal concentrations of 1 mg/ml methanol. A Clipeus™ C18, 5 μ, 150×4.6 mm column (P. J. Colbert Associates, Inc., Saint Louis, Mo.) was operated isocratically at 1 ml/min in 25% v/v methanol at 30° C. Runs were for 12 min with a theophylline retention time of about 5 min and caffeine at about 7 min at 270 nm. It was readily possible to detect an injected amount of 0.05 μg for these methylxanthines.

Table 3 compares caffeine concentrations determined in the Competition Caffeine-ELISA to those from our HPLC method and published values. The methods show good agreement. Reported values for coffee and decaffeinated coffee show a wide range which reflects differences in brands and brewing conditions.

TABLE 3

Caffeine Concentrations (μg/mL) in Various Beverages determined by Different Methods. The ELISA and HPLC values are the median of three determinations.

| Beverage | ELISA | HPLC | Literature |
|---|---|---|---|
| Regular coffee | 565 | 600 | 350-1200[1,2] |
| Decaf coffee | 28 | 30 | 20-26[2,3] |
| Coca-Cola Classic ® | 96 | 112 | 96[4] |
| Diet Coke ® | 132 | 156 | 129[4] |

[1]Lundsberg, L. S., Caffeine (1998) 213
[2]Bispo, M. S., et al., J. Chromatogr. Sci. (2002) 40: 45-48
[3]Internet address: ico.org/acoff/caffeine.htm
[4]Internet address: coca-cola.com/mail/goodanswer/utility.html

EXAMPLE 11

Removal of Caffeine from Solution

The ability of VSA2 to remove caffeine from solution was assessed. VSA2 still containing the His Tag (prior to thrombin cleavage) was coupled to a NiNTA agarose column via its N-terminus His Tag. Approximately 1 mg of antibody was bound to 1 ml of swollen agarose. One mg of a different unrelated protein which also contained a Histag was bound to a NiNTA agarose column as a control. Five μg of caffeine in 0.5 ml of PBS was passed over the column and then washed with 4 ml of PBS and 0.5 ml fractions collected. The amount of caffeine in the wash solutions was determined by absorbance at 273 nm and converted to amount of caffeine via comparison with the absorbance of standards (0, 2.5, 5, 10 ug).

The experiments were performed in duplicate and of the five μg added initially to the column, an average of 1.4 μg was recovered in the washing solutions indicating 3.6 μg of caffeine was bound to the column. Addition of a second 5 ug caffeine aliquot lead to only 0.6 ug additional bound caffeine. The control only showed 0.4 ug caffeine bound.

The caffeine bound to the column was eluted with 8 M urea, 100 mM sodium phosphate, 10 mM tris, pH 6.3 and 4.1 ug of caffeine came off the column which was in excellent agreement with the 4.2 ug which had originally bound to the column. No caffeine was eluted from the control column.

The ability of the VSA2 column to remove caffeine from solution was confirmed using HPLC (method previously described) to analyze the original caffeine solution put on the column and the fractions from the column washes. The HPLC analysis indicated that 3.8 μg of caffeine bound to the column in good agreement with the 4.2 μg using the UV method. The HPLC procedure could not be used to measure the caffeine eluted from the column due to the presence of 8 M urea.

The ability of VSA2 to remove caffeine from "decaffeinated" coffee was also assessed using brewed decaffeinated coffee (Seattle's Best™). By HPLC analysis, this batch of decaffeinated coffee had 30.8 μg/mL of caffeine. One hundred and sixty seven μL (5.15 μg caffeine) of the decaffeinated coffee was placed on the column and then the column washed as previously described and caffeine measured by HPLC in the 0.5 ml aliquots. 3.9 μg of caffeine was removed from the first decaffeinated coffee aliquot placed on the column and 0.5 μg from the second 167 μl aliquot. The total of 4.4 μg of caffeine removed by the column was very similar to the 4.2 μg removed by the column when caffeine was in a simple solution.

The above results indicate that the llama antibody is capable of removing caffeine from coffee and furthermore can remove caffeine from even "decaffeinated" coffee.

The invention claimed is:

1. An isolated camelized heavy chain $V_{HH}$ single-chain recombinantly produced antibody which comprises SEQ ID NO: 4.

2. An isolated, $V_{HH}$ single-chain recombinantly produced antibody which comprises SEQ ID NO: 5.

3. An isolated $V_{HH}$ single-chain recombinantly produced antibody which comprises SEQ ID NO: 2.

4. An isolated $V_{HH}$ single-chain recombinantly produced antibody which comprises SEQ ID NO: 3.

5. An isolated $V_{HH}$ single-chain recombinantly produced antibody which comprises SEQ ID NO: 1.

6. A lateral flow device having three reactive zones sequentially arranged in a same or substantially same plane wherein the first zone comprises a mobile, labeled caffeine-binding $V_{HH}$ antibody, the second zone comprises a stationary caffeine derivative that binds said $V_{HH}$ antibody and the third zone comprises a stationary polyclonal or monoclonal antibody or antibody fragment that binds said $V_{HH}$ antibody, wherein said labeled caffeine-binding $V_{HH}$ antibody includes the $V_{HH}$ antibody region in any one of SEQ ID NO's: 1-5.

7. The device of claim 6 which comprises a liquid flow-conducting strip or series of pads having a backing supporting the zones.

8. The device of claim 7 which further comprises a handle adjoining the third zone configured for the human hand.

9. The device of claim 6 wherein said stationary caffeine derivative is caffeine conjugated to a protein or a peptide.

10. A single step method for selectively detecting and/or quantifying caffeine in a fluid sample which comprises contacting a sample of said fluid with the device of claim 6 and detecting the presence, absence or amount of label in the second and/or third zone.

11. The method of claim 10 wherein the device is held vertically.

12. A kit useful to provide a point of use analytical qualitative determination of an amount of caffeine in a fluid sample which comprises the device of claim 6.

* * * * *